US006818673B2

(12) United States Patent
Ferguson

(10) Patent No.: US 6,818,673 B2
(45) Date of Patent: Nov. 16, 2004

(54) METHOD FOR PRODUCING SILICONE FOAM UTILIZING A MECHANICAL FOAMING AGENT

(75) Inventor: Terrell W. Ferguson, Georgetown, KY (US)

(73) Assignee: Radiant Holdings, LLC, Lexington, KY (US)

( * ) Notice: Subject to any disclaimer, the term of this patent is extended or adjusted under 35 U.S.C. 154(b) by 0 days.

(21) Appl. No.: 10/480,402

(22) PCT Filed: Aug. 23, 2002

(86) PCT No.: PCT/US02/27069

§ 371 (c)(1),
(2), (4) Date: Dec. 9, 2003

(87) PCT Pub. No.: WO03/024698

PCT Pub. Date: Mar. 27, 2003

(65) Prior Publication Data

US 2004/0167238 A1 Aug. 26, 2004

Related U.S. Application Data

(60) Provisional application No. 60/314,988, filed on Aug. 24, 2001.

(51) Int. Cl.[7] .................................................. C08J 9/26
(52) U.S. Cl. ............................ 521/61; 521/62; 521/154
(58) Field of Search ............................. 521/61, 62, 154

(56) References Cited

U.S. PATENT DOCUMENTS

| 3,293,663 | A |   | 12/1966 | Cronin |
| 4,157,424 | A |   | 6/1979  | Boutle |
| 4,195,639 | A |   | 1/1980  | Lee |
| 4,199,825 | A |   | 4/1980  | Knoche |
| 4,242,464 | A |   | 12/1980 | Boutle |
| 4,364,880 | A |   | 12/1982 | Howse |
| 4,401,492 | A |   | 8/1983  | Pfrommer |
| 4,405,360 | A |   | 9/1983  | Cardarelli |
| 4,600,551 | A |   | 7/1986  | Erb |
| 4,661,187 | A |   | 4/1987  | Beasley |
| 4,735,754 | A |   | 4/1988  | Buckner |
| 4,859,712 | A |   | 8/1989  | Cox |
| 4,889,744 | A |   | 12/1989 | Quaid |
| 4,892,544 | A | * | 1/1990  | Frisch ........................ 128/898 |
| 4,950,291 | A |   | 8/1990  | Mulligan |
| 5,681,572 | A |   | 10/1997 | Seare, Jr. |
| 5,798,065 | A | * | 8/1998  | Picha ......................... 264/46.4 |
| 5,855,606 | A |   | 1/1999  | Eaton |
| 5,993,716 | A |   | 11/1999 | Draenert |
| 6,156,065 | A |   | 12/2000 | Eaton |
| 6,187,043 | B1|   | 2/2001  | Ledergerber |
| 6,221,477 | B1| * | 4/2001  | Draenert ................... 428/307.3 |

\* cited by examiner

Primary Examiner—Morton Foelak
(74) Attorney, Agent, or Firm—King & Schickli, PLLC

(57) ABSTRACT

A method of producing silicone foam includes the step of adding a mechanical foaming agent to uncured silicone. The mechanical foaming agent is a plurality of solid bodies insoluble in the silicone. The method also includes the steps of curing the silicone and removing the mechanical foaming agent as intact solid bodies from the silicone thereby providing a silicone foam.

5 Claims, No Drawings

METHOD FOR PRODUCING SILICONE FOAM UTILIZING A MECHANICAL FOAMING AGENT

This patent application claims the benefit of U.S. Provisional Patent Application Ser. No. 60/314,988 filed on Aug. 24, 2001.

TECHNICAL FIELD

The present invention relates generally to the manufacture of silicone foam and, more particularly, to the manufacture of silicone foam utilizing a reusable mechanical foaming agent.

BACKGROUND OF THE INVENTION

Prosthetic devices are used for a number of purposes at various locations in the body. Many of these devices are implantable. One of the most common uses has been for augmenting or reconstructing the female breast. An example of a common breast prosthesis is disclosed in, for example, U.S. Pat. No. 3,293,663 to Cronin.

The Cronin prosthesis includes a flexible elastomeric container or envelope, typically formed from silicone that is filled with a soft gel, typically silicone gel or a saline solution or a combination of both.

It has been found that smooth envelope surfaces have a tendency to become encapsulated in fibrous scar tissue. The encapsulations are quite hard and in many instances frustrated the intended purpose of the prosthesis. As a consequence encapsulation sometimes requires a revision of the procedure. Such a revision means the implantation of another prosthesis. Unfortunately, this adds to patient distress and subjects the patient to the risks and expenses of the surgery for a second time.

In order to avoid or limit the scar tissue encapsulation problem, it has been found that an implant with a textured or roughened surface disorganizes the scar tissue and leads to improved results. Thus, silicone may be molded in geometric patterns on the outer surface of an implant to provide texturing as disclosed in U.S. Pat. No. 6,187,043 to Ledergerber. Silicone foam may also be employed for this purpose as disclosed in U.S. Pat. No. 4,859,712 to Cox.

More specifically, the Cox patent discloses a method for making a silicone skin for implantation where the overall density and depth of the foam may be carefully controlled beyond that possible when using chemical foaming agents. More specifically, crystalline material is embedded in a layer of uncured silicone. The silicone is then cured and a solvent is then used to dissolve the crystals out of the silicone thereby leaving an irregular surface. The size and amount of the crystals are varied to produce a desired surface texture or structure.

While the method disclosed in Cox is quite useful for customizing a silicone foam structure to meet the needs of any particular application, improvement is still possible. Specifically, the dissolving step and the step of subsequently drying or removing the solvent from the silicone foam are relatively time-consuming and therefore slow production rates. Further, it is necessary to recover the crystalline material from the solvent or continually provide a new source of crystalline material. Additionally, if the crystalline material is not recovered waste treatment is required in order to avoid contamination of the environment. The present invention relates to a method of producing a silicone foam which allows one to customize the foam to a particular application in a manner similar to that taught in the Cox patent yet totally avoids these other shortcomings.

SUMMARY OF THE INVENTION

In accordance with the purposes of the present invention as described herein an improved method is provided for producing silicone foam. The method includes the steps of adding a mechanical foaming agent in the form of a plurality of solid bodies to uncured silicone, curing the silicone and removing the mechanical foaming agent as intact solid bodies from the silicone thereby providing a silicone foam.

The method may be further defined as including the step of reusing the mechanical foaming agent to produce more silicone foam following the removing step. Further the method may include the selecting of the mechanical foaming agent from a group of materials consisting of metal, plastic, glass, cured silicone beads and mixtures thereof. Additionally, the solid bodies of mechanical foaming agent may have a width/diameter of between about 0.5 to about 8.0 mm. Further the mechanical foaming agent may be removed by pressing the solid bodies from the cured silicone foam.

DETAILED DESCRIPTION OF THE INVENTION

The present invention relates to a method of producing silicone foam which may be generally described as including the steps of adding a mechanical foaming agent to uncured silicone, curing the silicone and removing the mechanical foaming agent from the silicone thereby providing a silicone foam. In accordance with an important aspect of the present invention, the mechanical foaming agent is a plurality of solid bodies that are insoluble in the silicone.

Any appropriate solid material may be utilized for the mechanical foaming agent including but not limited to materials selected from a group consisting of metal, plastic, glass, cured silicone beads and mixtures thereof. The bodies may comprise substantially any shape, regular or irregular, spherical, cylindrical, tear-drop, pellet, bead, particulate, etc. The solid bodies of mechanical foaming agent typically have a width/diameter of between about 0.5 to about 8.0 mm.

The quantity, size and shape of the bodies of mechanical foaming agent may be varied to produce a silicone foam with differing physical properties such as density and resiliency. For example, by increasing the size of the mechanical foaming agent bodies used in the process the resulting silicone foam is made less resistant to linear deformation, i.e. flex increases. The density of the foam may be increased by the use of smaller more tightly packed bodies. A very soft foam may be made using bodies having a width/diameter of about 1 mm. The addition of silicone oil to the silicone (up to 40% by weight) increases the softness of the product. Thus, it should be appreciated that the silicone foam may be tailored to provide appropriate properties for any particular application.

In accordance with still another aspect of the present invention the method includes the step of reusing at least some of the mechanical foaming agent to produce more silicone foam following the removing step. As should be appreciated, following curing, the mechanical foaming agent may be removed by pressing the solid bodies from the cured silicone. In this way the mechanical foaming agent is removed from the silicone as intact solid bodies readily available for use again in the present method or process. Further, this physical removing or pressing of the solid bodies from the foam results in the forming of channels or pathways in the foam. These channels extend as discontinuities from the resting place of the individual solid bodies during formation of the foam to the outer surface of the foam through which the solid bodies are discharged. This creates a foam structure with unique physical characteristics, tactile properties closely mimicking living tissue, and enhanced ventilation.

Advantageously, the present invention avoids the use of any solvents, eliminates the necessity of any drying step, avoids the production of any waste materials and provides a foaming agent that is up to 100% reusable. These significant advantages are unavailable with any known prior art approach for producing silicone foam.

Of course, it should be realized that no chemicals, gases or other potentially hazardous agents are utilized to create the silicone foam product in the present method. Further the technique is applicable to all silicone compounds including condensation and platinum cure compounds. Advantageously, the present method provides consistent, repeatable results each time silicone foam is made. The texture, hardness, softness and cellular size may be easily regulated by simply changing the number, size and shape of the mechanical foaming agent bodies used to produce the silicone foam product. An integral layered product may also be produced. This is particularly useful when the silicone foam is utilized in the production of prostheses. The prostheses may be molded with a solid skin layer, a cellular foam layer to provide the prosthesis with the proper, life-like feel and a porous backing layer for anchoring the prosthesis to the dermis of the patient. Since each of the various layers is made from the same silicone compound the layers avoid any tendency to separate and they age at the same rate.

The silicone foam of the present invention may be utilized in the production of various prostheses including but not limited to breast (both implantable and nonimplantable), limb, digit, nose and ear prostheses. The silicone foam may also be used in the production of other, non-medical products for which silicone foam is an appropriate construction material. Such applications may be found, for example, in the bedding, furniture, automotive, marine and safety equipment industries to name just a few possibilities.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed:

1. A method of producing silicone foam, comprising:

adding a mechanical foaming agent to uncured silicone, said mechanical foaming agent being a plurality of solid bodies insoluble in said silicone;

curing said silicone; and removing said mechanical foaming agent as intact solid bodies from said silicone thereby providing a silicone foam.

2. The method of claim 1, further including reusing said mechanical foaming agent to produce more silicone foam following the removing step.

3. The method of claim 1, further including selecting said mechanical foaming agent from a group of materials consisting of metal, plastic, glass, cured silicone beads and mixtures thereof.

4. The method of claim 3, wherein said solid bodies of mechanical foaming agent have a width/diameter between about 0.5 and about 8.0 mm.

5. The method of claim 4, wherein said mechanical foaming agent is removed by pressing said solid bodies from said cured silicone.

* * * * *